United States Patent
Milnes et al.

(10) Patent No.: US 11,203,735 B2
(45) Date of Patent: Dec. 21, 2021

(54) HOSE ON WASTE FOOD MACHINE USED TO CLEAN FOOD PROCESSING MACHINE

(71) Applicants: Iain Milnes, Fremont, CA (US); Agile Johns, San Jose, CA (US)

(72) Inventors: Iain Milnes, Fremont, CA (US); Agile Johns, San Jose, CA (US)

(73) Assignee: Power Knot Inc., Fremont, CA (US)

( * ) Notice: Subject to any disclaimer, the term of this patent is extended or adjusted under 35 U.S.C. 154(b) by 589 days.

(21) Appl. No.: 15/817,116

(22) Filed: Nov. 17, 2017

(65) Prior Publication Data

US 2019/0153378 A1 May 23, 2019

(51) Int. Cl.

| | |
|---|---|
| *C12M 1/00* | (2006.01) |
| *C12M 1/06* | (2006.01) |
| *B08B 3/02* | (2006.01) |
| *B08B 9/08* | (2006.01) |
| *F26B 11/16* | (2006.01) |
| *C12M 1/26* | (2006.01) |
| *C12M 1/107* | (2006.01) |
| *C12M 1/33* | (2006.01) |

(52) U.S. Cl.
CPC ............ *C12M 39/00* (2013.01); *B08B 3/026* (2013.01); *B08B 9/0813* (2013.01); *C12M 21/04* (2013.01); *C12M 27/02* (2013.01); *C12M 33/00* (2013.01); *C12M 45/02* (2013.01); *F26B 11/16* (2013.01); *F26B 2200/02* (2013.01); *F26B 2200/04* (2013.01)

(58) Field of Classification Search
CPC ...... B08B 3/026; B08B 9/0813; C12M 21/04; C12M 27/02; C12M 33/00; C12M 39/00; C12M 45/02; F26B 11/16; F26B 2200/02; F26B 2200/04
See application file for complete search history.

(56) References Cited

U.S. PATENT DOCUMENTS

| | | | | |
|---|---|---|---|---|
| 6,110,727 A | * | 8/2000 | Widmer | C05F 17/939 435/262 |
| 6,149,033 A | * | 11/2000 | Poleshuk | B67D 7/12 222/75 |
| 8,118,948 B1 | * | 2/2012 | Szabo | B08B 3/026 134/111 |
| 2001/0031459 A1 | * | 10/2001 | Fahy | A01N 1/0247 435/1.3 |
| 2006/0102231 A1 | * | 5/2006 | Schiller | B65H 75/36 137/355.12 |
| 2006/0130884 A1 | * | 6/2006 | Liao | B08B 3/026 134/94.1 |

(Continued)

FOREIGN PATENT DOCUMENTS

| | | | | |
|---|---|---|---|---|
| EP | 0770575 A1 | * | 5/1997 | ............ B08B 3/026 |
| KR | 101418740 B1 | * | 7/2014 | |

OTHER PUBLICATIONS

Lee Woo Jin, "English machine translation of KR-101418740-B1". (Year: 2014).*

*Primary Examiner* — Liban M Hassan
(74) *Attorney, Agent, or Firm* — Patent Professional Corp.; Bao Tran (57) ABSTRACT

A system to process a waste food includes a housing; at least one drum enclosed in the housing where the waste food is mixed up and digested by microorganisms or dehydrated; and at least one cleaner incorporated in or on the machine to permit a jet of water to be turned on and off to clean the drum.

16 Claims, 5 Drawing Sheets

(56) References Cited

U.S. PATENT DOCUMENTS

| | | | | |
|---|---|---|---|---|
| 2007/0261719 A1* | 11/2007 | Amato | ............... | B08B 3/026 |
| | | | | 134/34 |
| 2008/0067270 A1* | 3/2008 | Strutz | ............... | B02C 25/00 |
| | | | | 241/36 |
| 2008/0210790 A1* | 9/2008 | Koh | ............... | C05F 17/20 |
| | | | | 241/33 |
| 2008/0259719 A1* | 10/2008 | Koh | ............... | B09B 3/00 |
| | | | | 366/138 |
| 2009/0311772 A1* | 12/2009 | Quinn | ............... | C12M 21/12 |
| | | | | 435/286.5 |
| 2013/0323824 A1* | 12/2013 | Koh | ............... | B02C 25/00 |
| | | | | 435/286.5 |
| 2014/0095108 A1* | 4/2014 | Milnes | ............... | G06Q 10/06 |
| | | | | 702/173 |

\* cited by examiner

FIG. 1

(PRIOR ART)

HOSE ON WASTE FOOD MACHINE USED TO CLEAN FOOD PROCESSING MACHINE

A. FIELD OF THE INVENTION

The present invention describes a hose on a waste food machine used to clean the waste food machine.

BACKGROUND

A waste food machine disposes of waste food or reduces its volume and weight; such machines have been in use about 20 years. Waste food machines may vary in size, with typical institutional machines processing from 20 kg per day to 3000 kg per day. Such devices may vary from about 50 cm wide to 400 cm wide. Many such machines are constructed mostly of stainless steel.

The waste food machine is a machine that is usually installed in an institutional kitchen. It is used by an organization or business that produces large quantities of waste food. The machines save or reduce the mess, cost, and inconvenience of sending the waste food to a landfill. When waste food is sent to a landfill it generally decomposes to methane (CH4) which is released to the atmosphere. CH4 is 84 times worse for the atmosphere than CO2. Businesses that generate waste food are realizing the implications of their waste food on the environment and the use of a waste food machine can help to significantly reduce their carbon footprint.

The present invention applies to any type of such waste food machine. There are two basic types of waste food machine: a wet type and a dry type.

With the wet type of machine, waste food is put into the machine where it is decomposed in an aerobic manner and the output is sent as grey water down the drain. With the dry type of machine, waste food is dehydrated reducing the volume significantly. The output can be sent to a landfill, sent for further processing to make compost, or used as a soil amendment.

Figure 1:
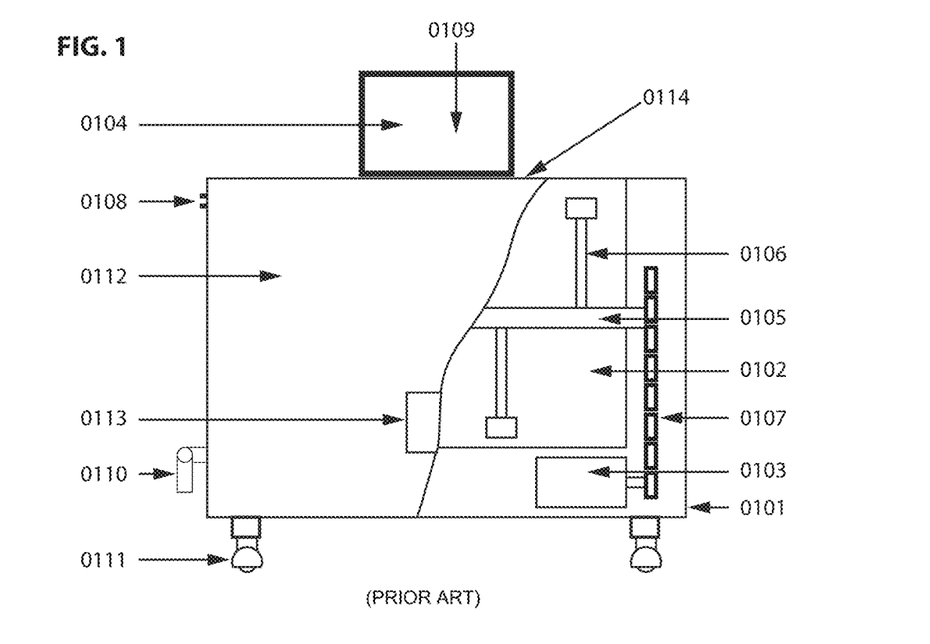
FIG. 1 shows a waste food machine.

FIG. 1 is a partially cut away side view of an exemplary waste food machine, in accordance with the prior art.

For a wet type of machine and referring to FIG. 1, a chassis 0101 supports a drum 0102 and a motor 0103. In general, waste food is put into drum 0102 through a door 0104. Motor 0103 drives a shaft 0105 with arms 0106 through a chain, belt, or system of gears 0107. Motor 0103 causes arms 0106 to rotate slowly (for example at about one revolution every five to 12 seconds) to mix old waste food with new waste food. Water may be added through an inlet 0108 to maintain the correct moisture content in drum 0102 for the decomposition process. The decomposition of the waste food may be accelerated by the addition of microorganisms, enzymes, or a blend of microorganisms and enzymes 0109 that are added periodically to drum 0102 either automatically or manually through door 0104.

In a typical machine, digested material exits the drum 0102 through a drain pipe 0110 and thereby the digested liquid and tiny particles may flow out of the machine to a drain. Chassis 0101 is often supported on supports 0111, of which there are typically four. In some machines, these supports may be combined with wheels to allow the machine to be moveable or the wheels may be separate. The supports may be the feet of load cells that allow the machine to weigh the waste food. An outer casing 0112 is usually made of stainless steel.

With a wet type of machine, the aerobic process of digestion when operating properly will not create CH4 and typically has no bad odors.

For a dry type of machine, the structure is similar to the wet type. However, water and microorganisms are not typically added to the machine. Usually, the machine is loaded with waste food, the door is closed, and the machine heats the waste food. Typically, the temperature is raised to 90° C. for six to 10 hours and a cycle takes about 18 hours. The machine may churn the waste during this process with the objective of breaking it into small pieces. At the end of the cycle, the dehydrated waste is emptied through an output door 0113, which is typically not present on the wet type of machine. The dehydrated waste is typically 5% to 10% of the original volume of waste food.

A hybrid type machine may start with a decomposition process similar to a wet type of machine, and, after a certain time, for example, 12 hours, the machine may then dry the remainder of the waste food similar to a dry type of machine.

When the waste food is placed into the drum and when the arms move the waste food inside the drum, some of the waste food can stick to the sides of the drum. It can remain there for some time and as new waste food is added, that waste food that had been stuck to the drum is pushed higher.

Figure 2:
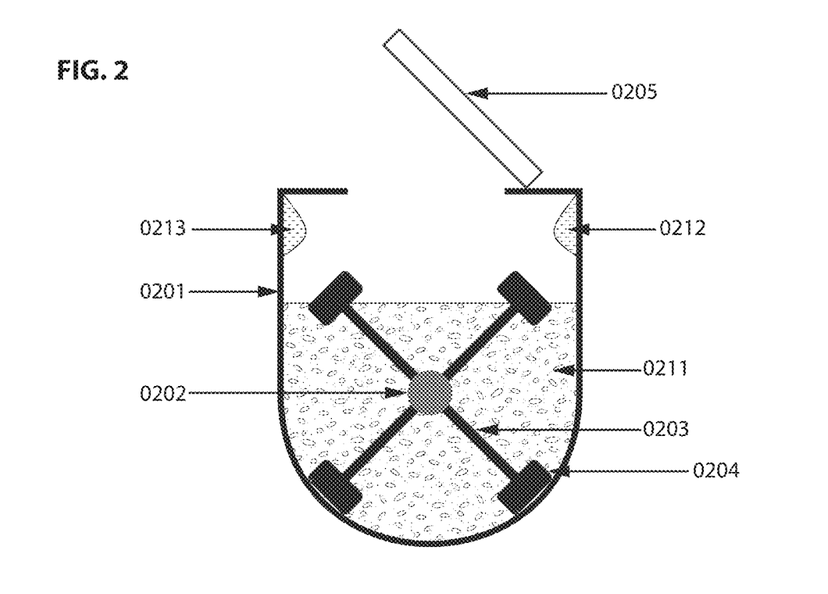
FIG. 2 is a cutaway side view of part of a waste food machine that shows the waste in the drum.

This is shown in FIG. 2 which shows a side view of part of a waste food machine. FIG. 2 shows the shaft 0202 with arms 0203 attached. At the end of the arms are paddles 0204. The arms and paddles rotate about the shaft slowly. The shaft may rotate clockwise and anti-clockwise at various times. The drum has a door 0205 through which waste food is added to the machine. The door 0205 is closed when the waste food machine is operating.

The waste food in the drum is shown as 0211 and in the case of a wet type of machine may be mixed with a medium that is used to house the microorganisms. The medium may be small chips made of wood, plastic, or some other material, and is normally porous and irregularly shaped.

Figure 3A:
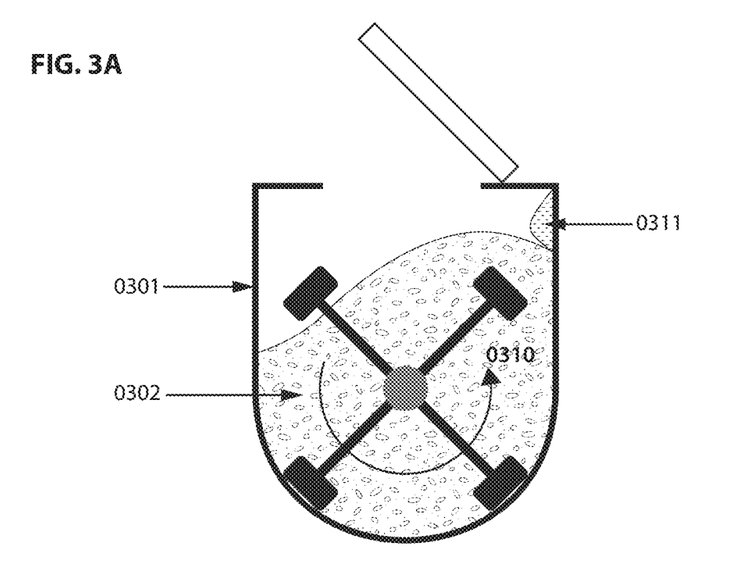
FIG. 3A and FIG. 3B are cutaway side views of part of a waste food machine that show the waste in the drum and the effect on the waste when the shaft is rotating one way or the other.
Figure 3B:
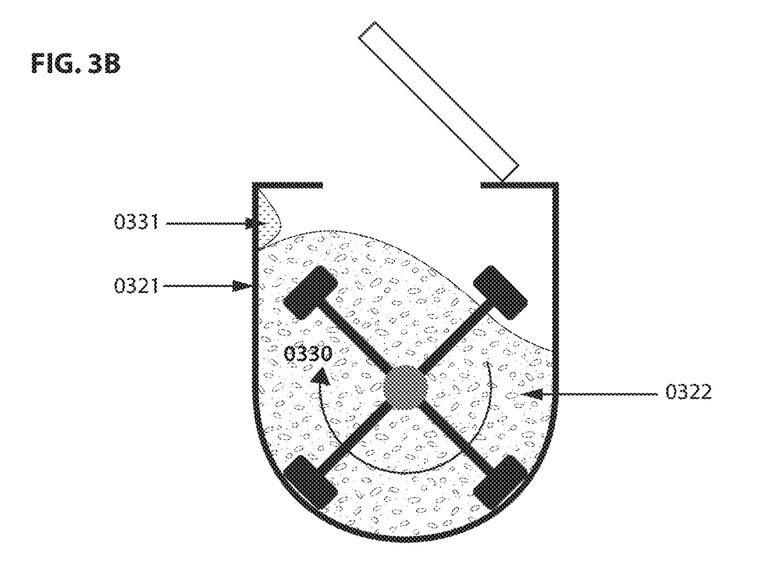

The mixture 0211 is not a liquid but comprises solid and semi-solid parts of waste food as well as the medium in the case of a wet type of machine. Therefore, as the shaft rotates, this mixture is pushed in one direction, and then pushed in the other direction as the shaft rotates in the opposite direction. This is shown in FIG. 3. FIG. 3A shows that when the shaft rotates in direction 0310 that the waste food is pushed up against the side of the drum 0301 to form a clump 0311. FIG. 3B shows that when the shaft rotates in the opposite direction 0330 that the waste food is pushed up against the side of the drum 0321 to form a clump 0331.

The result is that these clumps of waste food are on both sides of the drum as shown by 0212 and 0213 in FIG. 2.

The waste food within the clump 0212 and 0213 that is closest to the drum is deprived of oxygen and starts to decompose in an anaerobic manner, leading to smells from the drum. Further, the clump may grow mould or undesirable bacteria because it is no longer being mixed with the rest of the material in the drum.

It is therefore necessary to periodically clean the inside of the drum to remove these clumps of waste. This can be performed with a brush, towel, hose pipe, or a combination of these. With current implementations, the hose pipe may be plumbed externally to the waste food machine, that is, separate from the water inlet 0108 on FIG. 1.

SUMMARY

A system to process a waste food includes a housing; at least one drum enclosed in the housing where the waste food is mixed up and digested by microorganisms or dehydrated; and at least one cleaner incorporated in or on the machine to permit a jet of water to be turned on and off to clean the drum.

Implementations of the above aspect can include one or more of the following. The system incorporates the plumbing and the space for cleaner in or on a waste food machine. The cleaner generally has a hose pipe and a spray nozzle that are generally placed conveniently for a human operator of the waste food machine. The human operator can quickly and easily grab the spray nozzle and turn on a jet of water to clean the waste food machine and particularly to clean the inside of the drum.

Advantages of the system may include one or more of the following. The system provides a cleaner such as a hose incorporated into the design of a waste food machine. The hose allows the human operator to easily clean the waste food machine and the bin used to transport waste food to the machine, resulting in reduced smells and better sanitation. The hose can be easily accessed by the human operator and allows the human operator to clean the inside and outside of the waste food machine. For convenience and user safety, the hose and its associated plumbing should be kept within the space of the waste food machine.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangement shown.

Unless otherwise indicated illustrations in the figures are not necessarily drawn to scale and the graphical representation of objects does not limit the object to that shown.

DETAILED DESCRIPTION

Figure 4A:
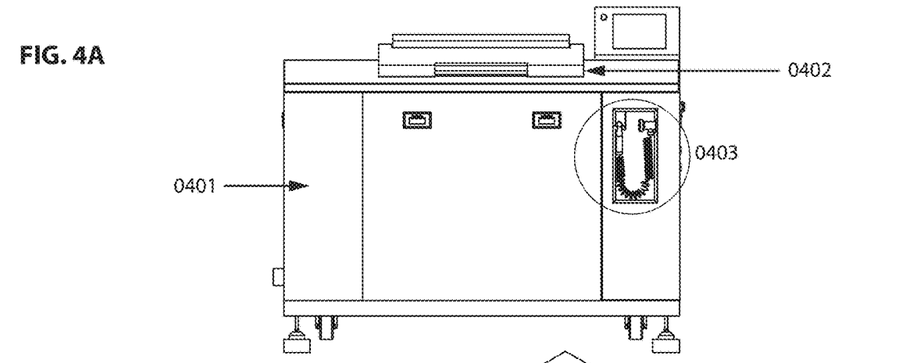
FIGS. 4A-4C show how the present invention can be incorporated into a waste food machine and the constituent parts of one embodiment of the present invention.
Figure 4B:
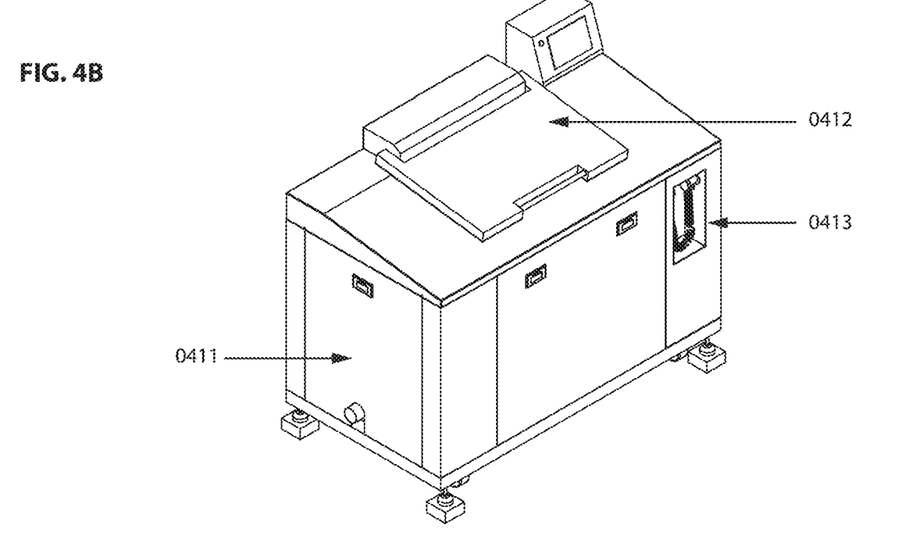
Figure 4C:
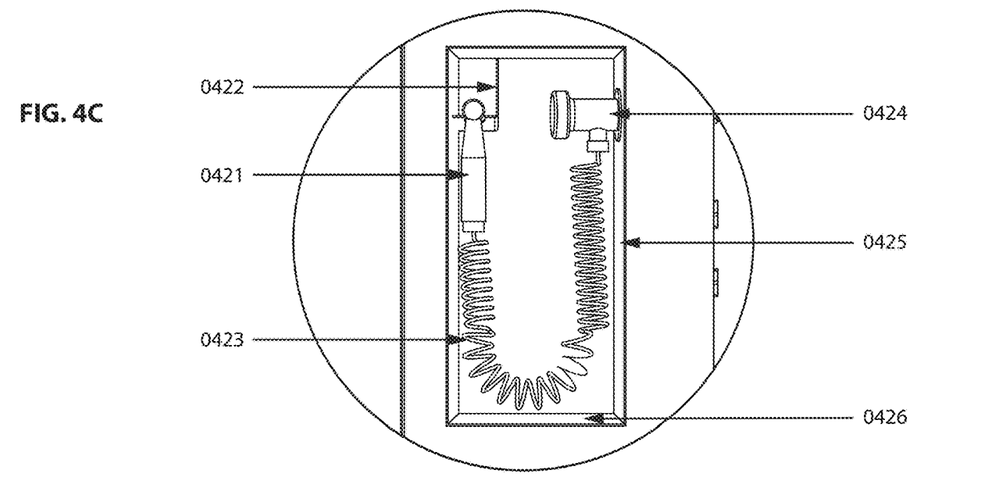

FIGS. 4A-4C show one way in which the present invention may be implemented. FIG. 4A is the front view of a waste food machine. The door 0402 is on top of the chassis 0401.

FIG. 4B is an isometric view of the same waste food machine with the chassis 0411 and the door 0412. The hose pipe and fittings are fitted into the chassis in a recess 0413. Although shown on the right of the waste food machine, this recess (and the fittings) could be anywhere on the chassis, including either side of the door 0412. The objective is that a human operator can access the fitting and, when the door is open, to be able to spray water about the inside of the drum. FIG. 4B shows that the apparatus of the present invention is fully recessed into the chassis of the waste food machine. While this is the most desirable approach, the present invention applies if the apparatus is partially recessed or not recessed at all.

FIG. 4C is a detail of the area identified as 0403 in FIG. 4A. The spray nozzle 0421 is held in place by a bracket 0422. While this is the most desirable approach, it would be possible to rest the spray nozzle on the bottom of the recess identified as 0413 in FIG. 4B.

The spray nozzle 0421 has a pipe 0423. The pipe 0423 is shown as a coiled pipe. While this is the most desirable approach, it would be possible to have a straight pipe that is wound around one or more brackets or that is fitted in a recess. It may also be possible to have the pipe retract into the chassis of the waste food machine in much the same way that an air hose at an automotive garage functions. Whichever method is used, the pipe should be long enough for the human operator to be able to position the spray nozzle inside the drum so that the jet of water can clean all the clumps identified as 0212 and 0213 in FIG. 2.

The pipe 0423 is attached to a fitting 0424. The fitting is shown on the right side of the recess, but it could be on any side of the recess or on the chassis of the waste food machine. This fitting passes the water from inside the chassis to outside the chassis. Internally, the fitting is connected to the water that is used to supply water to the drum, identified as 0108 in FIG. 1. While this is the most desirable approach, it would be possible to take the hose through a small opening and plumb it directly to the water circuit inside the chassis. It would also be possible to plumb this to a different water source inside the chassis, including a water source provided to the chassis solely for the purpose of the present invention.

It is desirable that the spray nozzle 0421 has a trigger to turn the water on and off. This will aid in usability. It is also desirable that fitting 0424 should have a tap to turn the water on and off. This will help in the event that the hose should become damaged. If the trigger on spray nozzle 0421 is omitted, it is necessary that there be another means of turning the water on and off, and that can be accomplished with a tap on fitting 0424. Equally, the spray nozzle may be omitted altogether, with the end of the pipe 0423 providing the necessary jet of water.

The sides of the recess 0413 are slanted so that the back of the recess is smaller than the opening of the recess. The right side that is sloping is identified as 0425 and the base that is sloping is identified as 0426. This provides a neat appearance and any water that is spilled in the recess will drain out of the recess instead of accumulating there. While the sloping sides, or at a minimum the sloping base 0426, provide the most desired approach, it is not mandatory for the present invention.

With the configuration shown in FIG. 4, it is possible for a human operator to open the door, grab the spray nozzle, extend the hose so the spray nozzle is inside the drum, and spray water around the sides of the drum. If water should spill from the spray nozzle as or after the nozzle is replaced on the bracket, that water will drain out of the recess.

Figures 5A, 5B, 5C:
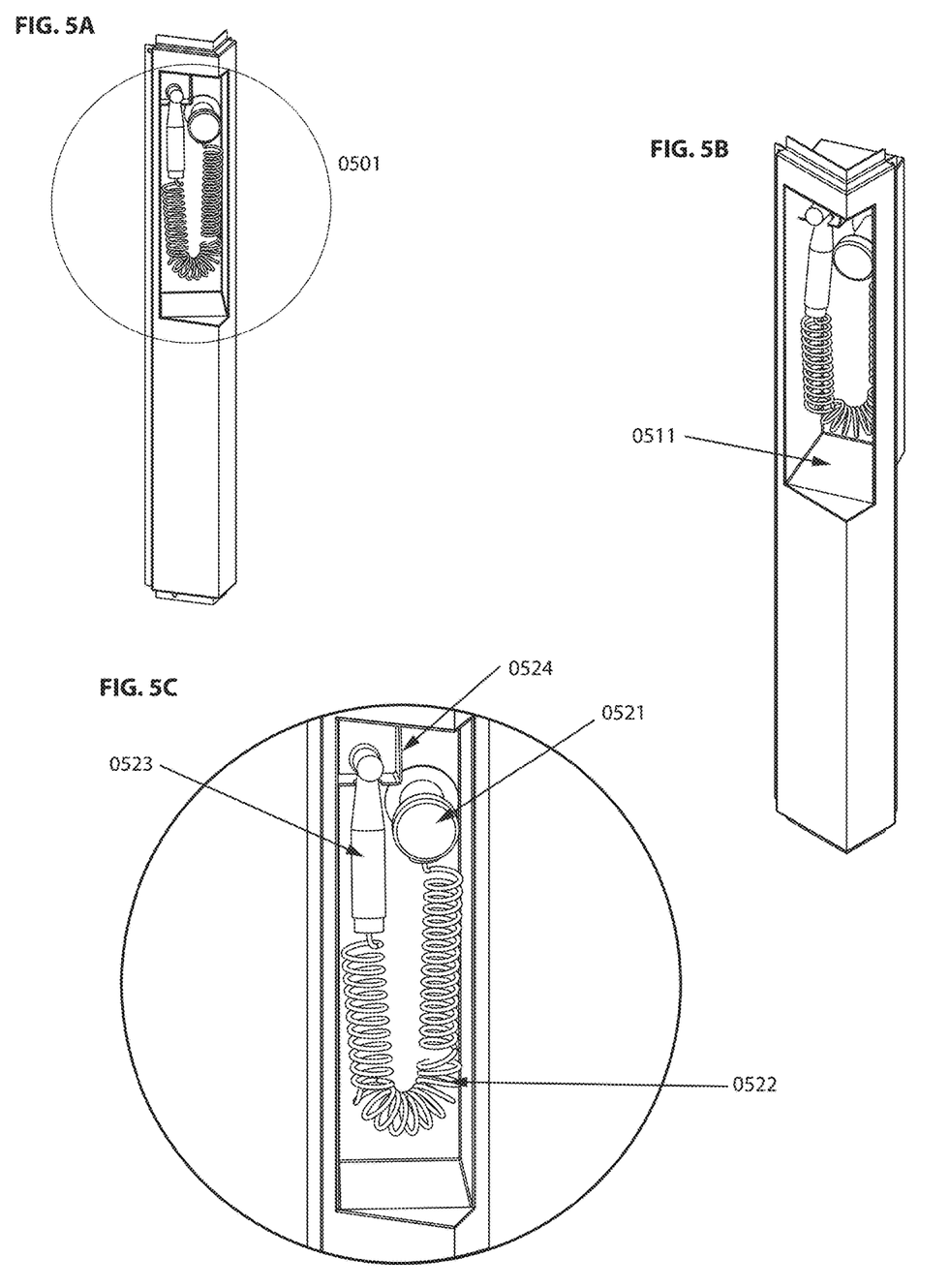
FIGS. 5A-5C show another example of how the present invention can be used, this time on the corner of a waste food machine instead of being within a panel.

A further example of the present invention is shown in FIG. 5. This figure shows only the corner panel of a waste food machine; its size relative to, and the method of incorporating it into, the waste food machine are immaterial to the present invention.

FIG. 5A shows an overview of the corner panel with the apparatus of the present invention circled as 0501 and shown in detail in FIG. 5C. FIG. 5B is a further view that shows the base of the recess 0511 sloping down so that water does not accumulate in the recess. In FIG. 5C the fitting 0521 connects to pipe 0522, the other end of which has the spray nozzle 0523. The spray nozzle is retained in bracket 0524.

Figure 6:
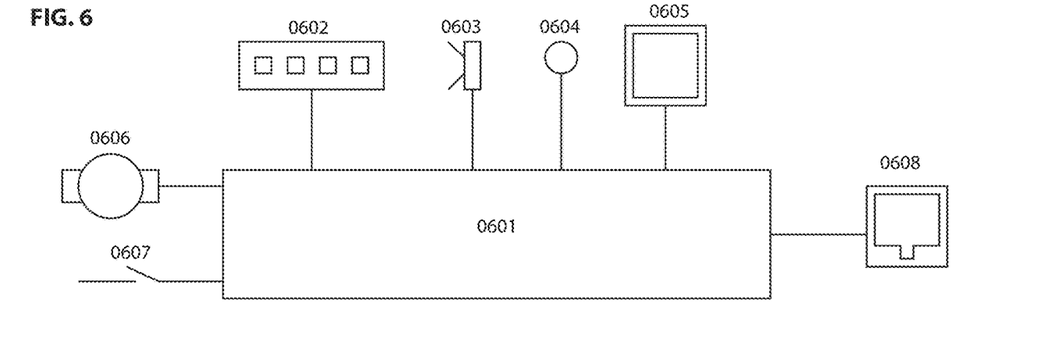
FIG. 6 shows a computer system that may be used in the waste food machine of FIG. 4.

In some embodiments, the waste food machine comprises a computer system that controls the operation of the machine, as shown in FIG. 6. This figure is not intended to be an exclusive demonstration of the functions of the computer system and the way it controls the waste food machine. FIG. 6 shows a processing system 0601. This comprises at least one processor, which may be an apparatus that executes programming instructions or preprogrammed logic. The processing system 0601 may contain one or more memory apparatus of one or more types. The processing system 0601 may connect with: none or more keypads, buttons, switches, or other input devices 0602; none or more audible devices, 0603; none or more lights such as LEDs or other kind, 0604; none or more displays, which may be monochrome or color, and which may be a touch screen, 0605; none or more motors, actuators, solenoids, valves, 0606; none or more sensors, switches, (including a switch to detect when the door 0104 is opened), and other various inputs, 0607; and none or more networks which may be wired, wireless, or optical, 0608. The particular implementation of the computer system and network is immaterial to the present invention; it may be implemented in any number of ways and contain any number of elements in addition to or instead of those mentioned above that may be applicable to the implementation of the particular waste food machine.

Figure 7:
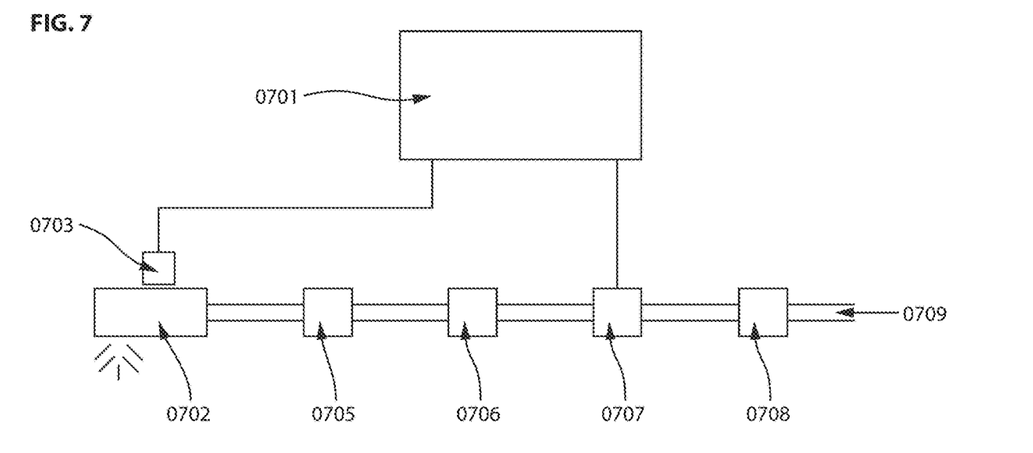
FIG. 7 shows how the computer system within the waste food machine can know that the hose of the present invention is being used.

Further, in certain example implementations, the computer system may monitor the usage of the spray nozzle 0523, and generate visual signals, audible signals, or both to remind human operators to use the spray nozzle 0523 to clean the waste food machine. An example of this is shown in FIG. 7 in which an example computer system as described above is shown as 0701. A spray nozzle 0702 takes water 0709 and can spray it into the drum of the waste food machine. A sensor 0703 may detect when the spray nozzle 0702 is removed from its bracket, shown for example, as 0422 and 0524. This sensor may be, for example, a mechanical switch, a hall effect switch, or a proximity sensor, and the sensor 0703 feeds a signal to the computer system 0701.

A tap 0705 is used to turn the water on or off. This tap may be incorporated into the spray nozzle to make it convenient for the user, may be combined with the fitting 0706, or may be separate. The fitting 0706 is equivalent to 0424 and carries the water from inside the chassis of the waste food machine to the outside.

A sensor 0707 may be fitted to detect if water is being used by the spray nozzle. This sensor may detect the flow of water through the pipe or it may detect that the pressure of water in the pipe has reduced. When the tap 0705 is turned on water exits the spray nozzle 0702 and a flow detector can detect this flow. Also, the pressure in the pipe will be reduced and a pressure detector can detect this. The signal from this sensor 0707 is fed to computer system 0701.

A one way valve 0708 may be fitted to the pipe. This may be needed for health and safety reasons, for example to prevent the backflow of water from the spray nozzle to the rest of the plumbing in the waste food machine or to the water supply in the facility. If sensor 0707 is a pressure sensor, the one way valve 0708 can isolate a drop in pressure in the pipe caused by other plumbing fittings inside the waste food machine to ensure better detection of the flow of water through the spray nozzle 0702.

If the waste food machine is equipped with a sensor that detects when the door 0104 is opened, the computer system can assume that the spray nozzle 0702 is being used to clean the inside of the drum when the door 0104 is opened. Conversely, the computer system can assume that the spray nozzle 0702 is being used to clean items other than inside the drum if the door 0104 is not opened concurrently.

In some embodiments, the computer system may monitor and calculate the usage of the spray nozzle, and generate audible and visual signals if the usage falls below one or more thresholds. In one embodiment, such threshold or thresholds may be fixed for the waste food machine during manufacturing. For example, the computer system in the waste food machine may be configured to remind the human operators to use the spray nozzle at least twice a day. In another embodiment, the threshold or thresholds may be configurable by one or more human operators, to better suit their requirements or preferences.

In a further embodiment, the computer system may automatically determine the required usage based on the operational status of the waste food machine. The operational status of the waste food machine may include the temperature inside the drum 0102, the amount of waste food currently inside the drum 0102, the amount of waste food that has been put into the drum over a certain prior time period, the rate of digestion of the waste food, or a combination of these parameters.

Figure 8A:
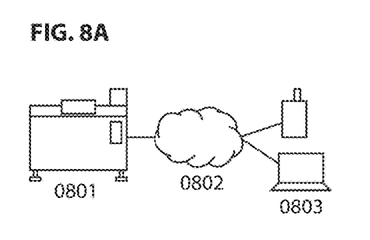
FIGS. 8A-8B show how the computer system within the waste food machine can inform users about the usage of the hose, either directly as in FIG. 8A or through an external computer system as in FIG. 8B.
Figure 8B:
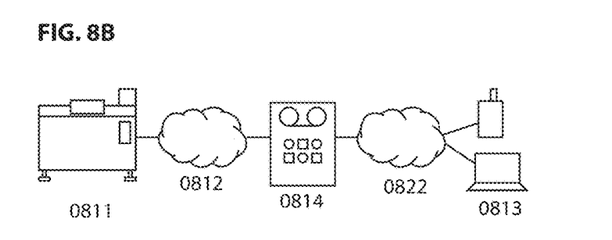

The computer system in the waste food machine can communicate the usage of the spray nozzle to the network 0608. This is shown in FIG. 8A. The computer system in the waste food machine 0801 will send one or more messages to network 0802. The messages are sent to, or made available by, one or more user devices 0803. The user devices 0803 can include a terminal, computer, or mobile phone. Alternatively, or concurrently, the communication can be sent to one or more computer systems elsewhere as shown in FIG. 8B. The computer system in the waste food machine 0811 will send one or more messages to network 0812. The messages are sent to an external computer system 0814 which makes information available by, sends messages to, or both, one or more user devices 0813 via network 0822. For example, the message may comprise an e-mail or SMS to one or more recipient. The networks 0812 and 0822 may be the same, different, or overlapping and may use the same or different means of communication.

The external computer system 0814 may have storage and may perform calculations on the usage of the spray nozzle. As such there may be more information about the usage of the spray nozzle available on the external computer system 0814 than is available on the computer system on the waste food machine 0811.

Report of usage, created by computer system 0801, 0811, or 0814 may include, for example, the number of times that the spray nozzle has been used period (such as day, week, or month), the duration of the usage of the spray nozzle, or the volume of water used.

Either the computer system in the waste food machine 0801 or 0811 or the computer system elsewhere 0814 can compare the time since last use, frequency of use, duration of use, or amount of water used of the spray nozzle to determine the type and timing of an alert to a user. For example, if the spray nozzle has not been used to clean the drum for a week, that may generate a simple reminder, but if the spray nozzle has not been used to clean the drum for a month that may generate an alert. These reminders and alerts may be made available on the waste food machine 0801 or 0811 (for example by using audible device 0603, light 0604, or display 0605), available for display on the external computer system 0814, or sent to a user's device 0803 or 0813.

If the external computer system 0814 is performing calculations on the usage of the spray nozzle, it may generate reminders or alerts as well as, or instead of, the computer system on the waste food machine 0811. The external computer system 0814 may send messages through network 0812 to computer system 0811 which can then announce the reminder or alert on the waste food machine.

If the external computer system 0814 has storage, it may be able to make available, or to automatically send, historical data to a user device 0813.

After a reminder or alert has been notified to a user and an operator then cleans the drum as detected by computer system 0701 described above, the reminder or alert may be automatically cleared, by computer system 0801, by computer system 0814, or both. Alternatively, the reminder or alert could be cleared by the user at the waste food machine by using for example an input device 0602.

Those skilled in the art will readily recognize, in light of and in accordance with the teachings of the present invention, that any of the foregoing steps may be suitably replaced, reordered, or removed, and additional steps may be inserted depending upon the needs of the particular application. Moreover, the prescribed methods or steps of the foregoing embodiments may be implemented using any physical and/or hardware system that those skilled in the art will readily know is suitable in light of the foregoing teachings. For any methods or steps described in the present application that can be carried out on a computing machine, a typical computer system can, when appropriately configured or designed, serve as a computer system in which those aspects of the invention may be embodied.

Using the spray nozzle to clean the waste food machine may introduce water into the drum. Therefore, in some embodiments, the computer system may record the duration for which the spray nozzle has been turned on, or the volume of water so introduced, and reduce the amount of water taken into the drum accordingly.

In some embodiments, the human operator may use the spray nozzle to clean the bin that is used to bring the waste food to the waste food machine. If the waste food machine is fitted with a computer system as described above, the computer system can discount usage of the spray nozzle for this or any other purpose when the door 0104 is closed. That is, such usage of the spray nozzle would not be considered part of the schedule to clean the inside of the drum.

The above describes a hose cleaner for a waste food machine. The hose allows the human operator to easily clean the waste food machine and the bin used to transport waste food to the machine, resulting in reduced smells and better sanitation. The hose can be easily accessed by the human operator and allows the human operator to clean the inside and outside of the waste food machine. It is preferred that the hose should be kept within the space of the waste food machine.

The advantages of the present invention can be achieved in an economical, practical, and facile manner. While preferred aspects and example configurations have been shown and described, it is to be understood that various further modifications and additional configurations will be apparent to those skilled in the art. It is intended that the specific embodiments and configurations herein disclosed are illustrative of the preferred nature of the invention, and should not be interpreted as limitations on the scope of the invention. While various embodiments of the invention have been described above, it should be understood that they have been presented by way of example only, and not by way of limitation. Although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

All references cited herein are incorporated herein by reference in their entirety. To the extent publications and patents or patent applications incorporated by reference contradict the disclosure contained in the specification, the specification is intended to supersede or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the erm" "including' should be read to mean "including, without limitation,' "including but not limited to,' or the like; the term "comprising" as used herein is synonymous with "including," "containing," or "characterized by," and is inclusive or open-ended and does not exclude additional, unlisted elements or method steps; the term "having" should be interpreted as "having at least;" the term "includes' should be interpreted as "includes but is not limited to;" the term "example" is used to provide exemplary instances of the item in discussion, not an exhaustive or limiting list thereof; adjectives such as "known," "normal," "standard," and terms of similar meaning should not be construed as limiting the item described to a given time period or to an item available as of a given time, but instead should be read to encompass known, normal, or standard technologies that may be available or known now or at any time in the future; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "any one of the items or any combination of the items" unless expressly stated otherwise.

With respect to the use of substantially any plural or singular terms herein, those having skill in the art can translate from the plural to the singular or from the singular to the plural as is appropriate to the context or application. The various singular or plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

All the features disclosed in this specification, including any accompanying abstract and drawings, may be replaced by alternative features serving the same, equivalent, or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing means for determining how much waste food is consumed by a waste food machine according to the present invention will be apparent to those skilled in the art. The invention has been described above by way of illustration, and the specific embodiments disclosed are not intended to limit the invention to the particular forms disclosed. For example, the particular implementation of the system may vary depending upon the particular type of processor used. The processors described in the foregoing were directed to internal implementations; however, similar techniques are to provide processors that are external to the machine. This processor may be sold as an option to a basic waste food machine. Implementations of the present invention comprising external processors are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A system to process a waste food, comprising:
    a housing movably mounted on wheels;
    at least one drum with one or more paddles enclosed in the housing to stir the waste food, wherein the drum comprises microorganisms to digest the waste food;
    at least one cleaner comprising a flexible hose pipe having a spray nozzle incorporated on the housing, the at least one cleaner configured to permit a jet of water to be turned on and off to clean the at least one drum; and
    an enclosure enclosing the at least one cleaner and mounted to a side, corner, or top of the housing, the enclosure defining a recess, wherein the at least one cleaner is housed within the recess, a support within the recess configured to support the spray nozzle, and wherein the recess includes a slanted base configured to direct and drain water from the recess through the opening, and wherein the flexible hose pipe and spray nozzle are enclosed within the recess and accessible from outside the housing through the opening.

2. The system of claim 1, wherein the at least one cleaner used to create the jet of water is coupled to a water source inside the housing.

3. The system of claim 1, comprising a switch to manually turn on or off the at least one cleaner.

4. The system of claim 1, wherein the at least one cleaner is configured to clean a bin used to bring waste food to the drum.

5. The system of claim 2, wherein the at least one cleaner includes a fitting to connect water from the inside of the housing.

6. The system of claim 1, further comprising a computer coupled to a plurality of sensors installed in or on the drum, the housing, or the at least one cleaner, the computer receiving measurements from the plurality of sensors and controls a plurality of actuators installed in the housing.

7. The system of claim 6, wherein the sensors comprise at least one door sensor, at least one temperature sensor, at least one load cell, and at least one water pressure sensor.

8. The system of claim 6, comprising at least one motor coupled to the at least one drum and at least one solenoid.

9. The system of claim 6, further comprising a water flow sensor, wherein the computer further monitors water jetting from the hose.

10. The system of claim 9, wherein the computer further compares a frequency, a timing, a duration, or water jetting with one or more thresholds, and if the frequency, timing, duration, or any combination is below one or more thresholds the computer generates reminders as visual or audible signals to a human operator to clean the drum.

11. The system of claim 10, wherein the one or more thresholds are preconfigured at a factory during manufacturing.

12. The system of claim 6, wherein the computer further generates reminders including visual or audible to an operator to clean the at least one drum at specific times.

13. The system of claim 6, wherein the computer further generates reports of water usage.

14. The system of claim 13, wherein the reports include a duration for which a jet of water is turned on.

15. The system of claim 13, wherein the computer transmits the generated reports on usage to a server coupled to a computer network.

16. The system of claim 6, wherein the computer adjusts the water taken into the drum based in part on the duration for which the jet of water is turned on or the amount of water used while the jet of water is turned on.

* * * * *